United States Patent [19]

Fabre et al.

[11] Patent Number: 4,547,504
[45] Date of Patent: Oct. 15, 1985

[54] SUBSTITUTED PHENYL PIPERAZINYL PYRROLIDIN-2-ONES AND RELATED COMPOUNDS USEFUL AS ANTI-DEPRESSANTS AND THEIR USE

[75] Inventors: Jean-Louis Fabre, Paris; Daniel Farge, Thiais; Claude James; Daniel Lave, both of Paris, all of France

[73] Assignee: Rhone-Poulenc Sante, Courbevoie, France

[21] Appl. No.: 558,775

[22] Filed: Dec. 6, 1983

[30] Foreign Application Priority Data

Dec. 7, 1982 [FR] France .................. 82 20492

[51] Int. Cl.$^4$ .................. C07D 403/04; C07D 401/04; A61K 31/495; A61K 31/445
[52] U.S. Cl. .................. 514/255; 544/372; 546/208; 514/326
[58] Field of Search .................. 544/372; 546/208; 424/250, 267

[56] References Cited
U.S. PATENT DOCUMENTS
4,247,549  1/1981  Ohnmacht et al. .................. 424/250

Primary Examiner—Donald G. Daus
Assistant Examiner—S. A. Gibson
Attorney, Agent, or Firm—Stevens, Davis, Miller & Mosher

[57] ABSTRACT

Pyrrolidine derivatives of the formula:

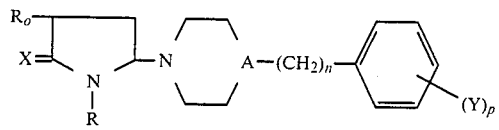

wherein X represents an oxygen or sulphur atom, R represents a hydrogen atom or an alkyl radical, $R_o$ represents a hydrogen atom, an alkyl radical or a phenyl radical optionally substituted by a halogen atom or by an alkyl, alkoxy, alkylthio or nitro radical, A represents a nitrogen atom or a radical =CH—, the symbol Y represents a hydrogen or halogen atom or an alkyl, alkoxy, alkylthio, alkylcarbonyl, nitro, amino, alkylcarbonylamino, alkylamino, dialkylamino, alkylsulphinyl, alkylsulphonyl, alkoxycarbonyl, cyano, trifluoromethyl, hydroxy, mercapto, alkylcarbonyloxy or alkylcarbonylthio radical, n represents zero or 1, and p represents 1, 2 or 3, it being understood that the alkyl and alkoxy radicals, and alkyl and alkoxy moieties of any of the aforementioned groups, contain from 1 to 4 carbon atoms are new therapeutically useful compounds, more particularly useful as antidepressants.

14 Claims, No Drawings

SUBSTITUTED PHENYL PIPERAZINYL PYRROLIDIN-2-ONES AND RELATED COMPOUNDS USEFUL AS ANTI-DEPRESSANTS AND THEIR USE

The present invention relates to new therapeutically useful pyrrolidine derivatives, to processes for their preparation and pharmaceutical compositions containing them.

The pyrrolidine derivatives of this invention are those compounds of the general formula:

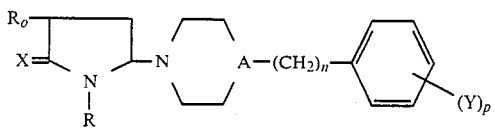

(wherein X represents an oxygen or sulphur atom, R represents a hydrogen atom or an alkyl radical, $R_o$ represents a hydrogen atom, an alkyl radical or a phenyl radical optionally substituted by a halogen atom or by an alkyl, alkoxy, alkylthio or nitro radical, A represents a nitrogen atom or a radical =CH—, the symbol Y represents a hydrogen or halogen atom or an alkyl, alkoxy, alkylthio, alkylcarbonyl, nitro, amino, alkylcarbonylamino, alkylamino, dialkylamino, alkylsulphinyl, alkylsulphonyl, alkoxycarbonyl, cyano, trifluoromethyl, hydroxy, mercapto, alkylcarbonyloxy or alkylcarbonylthio radical, n represents zero or 1, and p represents 1, 2 or 3, it being understood that the alkyl and alkoxy radicals, and alkyl and alkoxy moieties of any of the aforementioned groups, have straight- or branched-chains and contain from 1 to 4 carbon atoms) and their acid addition salts.

When the symbol p represents 2 or 3 the atoms or radicals represented by the symbols Y may be the same or different.

According to a feature of the present invention the pyrrolidine derivatives of general formula I, wherein X represents an oxygen atom and the other symbols are as hereinbefore defined, are obtained by the process which comprises reacting a compound of the general formula:

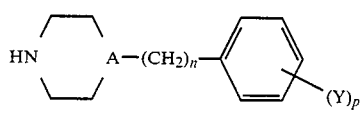

(wherein A, Y, n and p are as hereinbefore defined) with a pyrrolidin-2-one of the general formula:

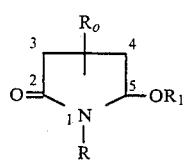

wherein R and $R_o$ are as hereinbefore defined and $R_1$ represents a straight- or branched-chain alkyl radical containing 1 to 4 carbon atoms, preferably ethyl.

The reaction is generally carried out without a solvent at a temperature between 70° and 180° C., or in an inert organic solvent, such as an aromatic hydrocarbon (e.g. xylene), at the reflux temperature of the reaction mixture, the alcohol formed optionally being removed.

Depending on the nature of the substituent(s) Y in the compound of general formula II, it may be advantageous to protect the functional group of the said substituent(s) before carrying out the reaction with the pyrrolidin-2-one of general formula III, the functional group(s) being freed after the condensation reaction. The blocking and unblocking can be carried out by the usual methods which are known to those skilled in the art and which do not affect the rest of the molecule.

The starting materials of general formula III can be obtained by reducing a corresponding pyrrolidine-2,5-dione of the general formula:

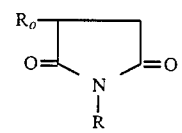

(wherein R and $R_o$ are as hereinbefore defined), the reduction being carried out in an alcohol of the general formula $R_1OH$, wherein $R_1$ is as hereinbefore defined. The reduction is advantageously carried out by means of an alkali metal borohydride in the presence of hydrogen chloride, as described by J. C. HUBERT, J. B. P. A. WIJNBERG and W. N. SPECKAMP, Tetrahedron, 31, 1437 (1975).

When $R_o$ is other than a hydrogen atom, the reduction takes place indiscriminately at one or other of the carbonyl groups of the pyrrolidinedione of general formula IV to give a product of general formula III in the form of a mixture of compounds in which the substituent $R_o$ is in the 3-position or in the 4-position of the pyrrolidine ring. In general, the mixture can be used as such to no disadvantage in the subsequent synthesis; its use does not detract from the purification of the final product of general formula I.

According to another feature of the invention the pyrrolidine derivatives of general formula I, wherein $R_o$, A, Y, n and p are as hereinbefore defined, X represents an oxygen atom and R represents an alkyl radical, are advantageously prepared by the process which comprises reacting a compound of the general formula:

R'Z    V (wherein R' represents a straight- or branched-chain alkyl radical containing 1 to 4 carbon atoms, and Z represents a halogen atom or a reactive ester radical such as mesyloxy or tosyloxy) with a pyrrolidine derivative of general formula I wherein $R_o$, A, Y, n and p are as hereinbefore defined and R represents a hydrogen atom, i.e., a pyrrolidine derivative of the general formula:

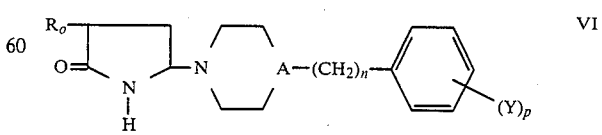

wherein the various symbols are as hereinbefore defined.

The reaction is generally carried in an anhydrous organic solvent, such as dimethylformamide, in the presence of a condensation agent such as an alkali metal hydride, at a temperature between 0° and 60° C.

When the substituent Y in the compound of general formula VI has a functional group which can be alkylated, it is advantageous to block the functional group of such a substituent before reaction with the reactive alkyl ester of general formula V. The blocking and subsequent unblocking of the functional group can be carried out by the usual methods which are known to those skilled in the art and which do not effect the rest of the molecule.

According to another feature of the invention the pyrrolidine derivatives of general formula I, wherein X represents a sulphur atom and the other symbols are as hereinbefore defined, are obtained by the process which comprises thionating a corresponding pyrrolidine derivative of general formula I wherein X represents an oxygen atom and the other symbols are as hereinbefore defined, i.e. a compound of the general formula:

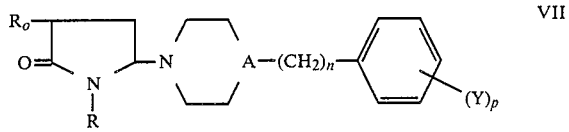

VII wherein the various symbols are as hereinbefore defined,

The thionation is generally carried out by means of phosphorus pentasulphide in an organic solvent, such as toluene, dioxan or 1,2-dimethoxyethane, at a temperature of about 100° C. or, preferably, by means of LAWESSON'S reagent [viz. 2,4-bis-(4-methoxyphenyl)-1,3,2,4-dithiadiphosphetane-2,4-dithione] in an organic solvent, such as toluene, at a temperature of about 50° C., or in an organic solvent, such as 1,2-dimethoxyethane or hexamethylphosphoramide, at a temperature of about 20° C.

When the substituent Y in the compound of general formula VII has a functional group sensitive to thionation, this functional group will have to be protected beforehand by a labile protecting group in accordance with the usual techniques known to those skilled in the art.

The pyrrolidine derivatives of general formula I obtained by the hereinbefore described processes can be purified by the usual methods, such as crystallisation, chromatography or successive extractions in an acid or basic medium.

The pyrrolidine derivatives of general formula I may be converted by known methods into acid addition salts. (By the term 'known methods' is meant methods heretofore used or described in the chemical literature). The acid addition salts may be obtained by reacting the pyrrolidine derivative with an acid in an organic solvent such as an alcohol, a ketone, an ester or a chlorinated hydrocarbon. The salt which is formed is precipitated, if necessary after concentration of the solution, and is isolated by filtration or decantation.

The pyrrolidine derivatives of general formula I and their acid addition salts have valuable pharmacological properties which make them useful as antidepressants.

They have been shown to be active as antidepressants, in particular in the test for the antagonistic action towards the depression induced by tetrabenazine in rats at doses between 1 and 100 mg/kg animal body weight, administered subcutaneously or orally.

The 50% lethal dose, $LD_{50}$, is generally between 100 and 900 mg/kg animal body weight, administered orally to mice.

U.S. Pat. No. 4,247,549 has disclosed piperazine-1-carboxylic acid esters which possess antidepressive and analgesic activities. However, the products disclosed in the United States patent do not lead one to the pyrrolidine derivatives of the present invention. Furthermore, the pyrrolidine derivatives of the present invention have more pronounced antidepressive properties.

Of particular value are the pyrrolidine derivatives of general formula I wherein X represents an oxygen or sulphur atom, $R_o$ represents a hydrogen atom, R represents a hydrogen atom or an alkyl radical, A represents a nitrogen atom or a radical =CH—, Y represents a hydrogen or halogen atom or an alkyl, alkoxy, alkylcarbonyl, nitro or trifluoromethyl radical, n represents zero or 1 and p represents 1.

Of more particular value are the pyrrolidine derivatives of general formula I wherein X represents an oxygen atom, $R_o$ and R each represent a hydrogen atom, A represents a nitrogen atom, Y represents a hydrogen or halogen atom or an alkyl, alkoxy, alkylcarbonyl or nitro radical, n represents zero and p represents 1.

Of outstanding importance are 5-(4-phenylpiperazin-1-yl)pyrrolidin-2-one, 5,[4-(2-methylphenyl)piperazin-1-yl]pyrrolidin-2-one, 5-[4-(4-chlorophenyl)piperazin-1-yl]pyrrolidin-2-one, 5-[4-(4-methoxyphenyl)piperazin-1-yl]pyrrolidin-2-one, 5-[4-(4-acetylphenyl)piperazin-1-yl]pyrrolidin-2-one, 5-[4,(3-trifluoromethylphenyl)piperazin-1-yl]pyrrolidin-2-one and 5-[4-(4-nitrophenyl)-piperazin-1-yl]pyrrolidin-2-one, and their acid addition salts.

For medicinal use, the pyrrolidine derivatives of general formula I can be employed as such or, optionally, in the form of pharmaceutically-acceptable acid addition salts, i.e. salts which are non-toxic at the use doses. Examples of pharmaceutically-acceptable acid addition salts are salts with inorganic acids (such as the hydrochlorides, sulphates, nitrates and phosphates) or with organic acids (such as the acetates, propionates, succinates, benzoates, fumarates, maleates, methanesulphonates, isethionates, theophyllineacetates, salicylates, phenolphthalinates and methylene-bis-$\beta$-hydroxynaphthoates) or substituted derivatives thereof.

The following Examples, which are given without implying a limitation, show how the invention can be put into practice.

EXAMPLE 1

A mixture of 5-ethoxypyrrolidin-2-one (10.4 g) and 4-phenylpiperazine (19.4 g) is heated for 1 hour 15 minutes at a temperature between 124° C. and 130° C., with stirring. After the reaction mixture has cooled, ethanol (30 cc) is added in order to suspend the solid obtained. The resulting crystals are filtered off, washed 3 times with ethanol (30 cc in total) and then 3 times with diethyl ether (75 cc in total) and dried under reduced pressure (20 mm Hg; 2.7 kPa) at a temperature of about 20° C. in the presence of potassium hydroxide pellets. This gives a crude product (15.8 g) melting at 206° C. This product is dissolved in boiling methanol (350 cc); the solution is treated with decolorising charcoal (1 g) and filtered hot. The filtrate is cooled at a temperature of about 4° C. for 1 hour. The crystals which have appeared are filtered off, washed 3 times with methanol (75 cc in total) and then 3 times with diethyl ether (75 cc in total) and dried under reduced pressure (20 mm Hg;

2.7 kPa) at a temperature of about 20° C. in the presence of potassium hydroxide pellets. This gives 5-(4-phenyl-piperazin-1-yl)pyrrolidin-2-one (12.1 g) in the form of white crystals melting at 210° C.

The 5-ethoxypyrrolidin-2-one can be prepared as described by J. C. HUBERT, J. B. P. A. WIJNBERG and W. N. SPECKAMP [Tetrahedron, 31, 1437 (1975)].

EXAMPLE 2

A mixture of 5-ethoxypyrrolidin-2-one (7.75 g) and 1-(2-methylphenyl)piperazine (10.6 g) is heated for 2 hours at a temperature between 127° C. and 140° C., with stirring, the ethanol formed being distilled off. After the reaction mixture has cooled, the solid obtained is filtered off, washed 4 times with ethyl acetate (35 cc in total) and dried under reduced pressure (20 mm Hg; 2.7 kPa) at a temperature of about 20° C. in the presence of potassium hydroxide pellets. This gives a crude product (12.45 g). This product is dissolved in boiling acetonitrile (150 cc); the solution is treated with decolorising charcoal (1 g) and filtered hot. The filtrate is cooled at a temperature of about 4° C. for 16 hours. The resulting crystals are filtered off, washed 3 times with acetonitrile cooled to a temperature of about 4° C. (30 cc in total) and dried under reduced pressure (20 mm Hg; 2.7 kPa) at a temperature of about 20° C. in the presence of potassium hydroxide pellets. This gives 5-[4-(2-methylphenyl)piperazin-1-yl]pyrrolidin-2-one (9.95 g) in the form of white crystals melting at 166° C.

EXAMPLE 3

A mixture of 5-ethoxypyrrolidin-2-one (12.9 g) and 1-(4-fluorophenyl)piperazine (18 g) is heated for 45 minutes at a temperature between 155° C. and 169° C., with stirring, the ethanol formed being distilled of. After the reaction mixture has cooled the solid obtained is filtered off, washed 4 times with ethyl acetate (40 cc in total) and dried under reduced pressure (20 mm Hg; 2.7 kPa) at a temperature of about 20° C. in the presence of potassium hydroxide pellets. This gives a crude product (20.1 g) melting at 170° C. This product is dissolved in boiling ethyl acetate (800 cc); the solution is treated with decolorising charcoal (1 g) and filtered hot. The filtrate is cooled at a temperature of about 4° C. for 3 days. The resulting crystals are filtered off, washed twice with ethyl acetate (20 cc in total) and dried under reduced pressure (20 mm Hg; 2.7 kPa) at a temperature of about 20° C. in the presence of potassium hydroxide pellets. This gives 5-[4-(4-fluorophenyl)piperazin-1-yl]pyrrolidin-2-one (17.6 g) in the form of white crystals melting at 180° C.

EXAMPLE 4

A mixture of 5-ethoxypyrrolidin-2-one (9.6 g) and 1-(4-chlorophenyl)piperazine (14.7 g) is heated for 1 hour 15 minutes at a temperature between 127° C. and 136° C., with stirring, the ethanol formed being distilled off. After the reaction mixture has cooled, the solid obtained is filtered off, washed 3 times with ethyl acetate (25 cc in total) and dried under reduced pressure (20 mm Hg; 2.7 kPa) at a temperature of about 20° C. in the presence of potassium hydroxide pellets. This gives a crude product (15.35 g) melting at 202° C. This product is dissolved in boiling ethanol (650 cc); the solution is treated with decolorising charcoal (1 g) and filtered hot. The filtrate is cooled at a temperature of about 4° C. for 3 hours. The resulting crystals are filtered off, washed 3 times with ethanol (150 cc in total) cooled to a temperature of about 4° C., and dried under reduced pressure (20 mm Hg; 2.7 kPa) at a temperature of about 20° C. in the presence of potassium hydroxide pellets. This gives 5-[4-(4-chlorophenyl)-piperazin-1-yl]pyrrolidin-2-one (12.5 g) in the form of white crystals melting at 209° C.

EXAMPLE 5

A mixture of 5-ethoxypyrrolidin-2-one (7.75 g) and 1-(3-chlorophenyl)piperazine (11.8 g) is heated for 2 hours 35 minutes at a temperature between 136° C. and 140° C., with stirring, the ethanol formed being distilled off. After the reaction mixture has cooled, the solid obtained is filtered off, washed 3 times with ethyl acetate (30 cc in total) and then twice with diethyl ether (50 cc in total) and dried under reduced pressure (20 mm Hg; 2.7 kPa) at a temperature of about 20° C. in the presence of potassium hydroxide pellets. This gives a crude product (13.3 g). This product is dissolved in boiling ethanol (105 cc); the solution is treated with decolorising charcoal (1 g) and filtered hot. The filtrate is cooled at a temperature of about 4° C. for 16 hours. The resulting crystals are filtered off, washed 3 times with ethanol (30 cc in total) cooled to a temperature of about 4° C., and dried under reduced pressure (20 mm Hg; 2.7 kPa) at a temperature of about 20° C. in the presence of potassium hydroxide pellets. This gives 5-[4-(3-chlorophenyl)piperazin-1-yl]pyrrolidin-2-one (11.15 g) in the form of beige crystals melting at 158° C.

EXAMPLE 6

A mixture of 5-ethoxypyrrolidin-2-one (7.75 g) and 1-(2-chlorophenyl)piperazine (11.8 g) is heated for 1 hour at a temperature between 137° C. and 145° C., with stirring, the ethanol formed being distilled off. After the reaction mixture has cooled, the solid obtained is filtered off, washed 4 times with ethyl acetate (40 cc in total) and dried under reduced pressure (20 mm Hg; 2.7 kPa) at a temperature of about 20° C. in the presence of potassium hydroxide pellets. This gives a crude product (12.45 g) melting at 192° C. This product is dissolved in boiling ethanol (260 cc); the solution is treated with decolorising charcoal (1 g) and filtered hot. The filtrate is cooled at a temperature of about 4° C. for 2 hours. The resulting crystals are filtered off, washed twice with ethanol (20 cc in total) cooled to a temperature of about 4° C., and dried under reduced pressure (20 mm Hg; 2.7 kPa) at a temperature of about 20° C. in the presence of potassium hydroxide pellets. This gives 5-(4-(2-chlorophenyl)piperazin-1-yl]pyrrolidin-2-one (10.55 g) in the form of white crystals melting at 198° C.

EXAMPLE 7

A mixture of 5-ethoxypyrrolidin-2-one (7.75 g) and 1-(4-methoxyphenyl)piperazine (11.55 g) is heated for 1 hour 10 minutes at a temperature of about 140° C., with stirring, the ethanol formed being distilled off. After the reaction mixture has cooled, the solid obtained is filtered off, washed 3 times with ethyl acetate (20 cc in total) and dried under reduced pressure (20 mm Hg; 2.7 kPa) at a temperature of about 20° C. in the presence of potassium hydroxide pellets. This gives a crude product (12.5 g) melting at 184° C. This product is dissolved in boiling acetonitrile (245 cc); the solution is treated with decolorising charcoal (1 g) and filtered hot. The filtrate is cooled at a temperature of about 4° C. for 16 hours. The resulting crystals are filtered off, washed twice with acetonitrile (20 cc in total) and dried under reduced pressure (20 mm Hg; 2.7 kPa) at a temperature of about 20° C. in the presence of potassium hydroxide pellets. This gives 5-[4-(4-methoxyphenyl)-piperazin-1-yl]pyrrolidin-2-one (10.9 g) in the form of white crystals melting at 189° C.

EXAMPLE 8

A mixture of 5-ethoxypyrrolidin-2-one (7.75 g) and 1-(4-acetylphenyl)piperazine (12.26 g) is heated for 1 hour 40 minutes at a temperature between 126° C. and 140° C., with stirring, the ethanol formed being distilled off. After the reaction mixture has cooled, the solid obtained is filtered off, washed 3 times with ethyl acetate (20 cc in total) and dried under reduced pressure (20 mm Hg; 2.7 kPa) at a temperature of about 20° C. in the presence of potassium hydroxide pellets. This gives a crude product (15.6 g) melting at 210° C. This product is dissolved in boiling butanol (80 cc); the solution is treated with decolorising charcoal (1 g) and filtered hot. The filtrate is cooled at a temperature of about 4° C. for 16 hours. The resulting crystals are filtered off, washed twice with butanol (20 cc in total) cooled to a temperature of about 4° C. and then 3 times with diisopropyl ether (60 cc in total), and dried under reduced pressure (20 mm Hg; 2.7 kPa) at a temperature of about 20° C. in the presence of potassium hydroxide pellets. This gives a product (12.1 g) melting at 210° C. This product (11.5 g) is taken up in a 0.5N aqueous solution of hydrochloric acid (80 cc). The solution is treated with decolorising charcoal (1 g) and filtered; the filtrate is cooled to a temperature of about 4° C. and rendered alkaline with a normal aqueous solution of sodium hydroxide (50 cc). After 10 minutes at a temperature of about 4° C., the resulting crystals are filtered off, washed 3 times with distilled water (30 cc in total) cooled to a temperature of about 4° C., and dried under reduced pressure (20 mm Hg; 2.7 kPa) at a temperature of about 20° C. in the presence of potassium hydroxide pellets. This gives a product (9.7 g) melting at 180° C. This product is dissolved in boiling butanol (80 cc) and the solution obtained is treated with decolorising charcoal (1 g) and filtered hot. The filtrate is cooled at a temperature of about 4° C. for 1 hour. The resulting crystals are filtered off, washed twice with butanol (20 cc in total) and dried under reduced pressure (20 mm Hg; 2.7 kPa) at a temperature of about 20° C. in the presence of potassium hydroxide pellets. This gives 5-[4-(4-acetylphenyl)piperazin-1-yl]pyrrolidin-2-one (6.7 g) in the form of yellow crystals melting at 199° C.

EXAMPLE 9

A mixture of 5-ethoxypyrrolidin-2-one (7.75 g) and 4-benzylpiperazine (11.1 g) is heated for 1 hour 10 minutes at a temperature between 140° and 145°, with stirring, the ethanol formed being distilled off. After the reaction mixture has cooled, the solid obtained is suspended in ethyl acetate (40 cc), filtered off, washed 3 times with ethyl acetate (25 cc in total) and dried under reduced pressure (20 mm Hg; 2.7 kPa) at a temperature of about 20° C. in the presence of potassium hydroxide pellets. This gives a crude product (11.9 g) melting at 159° C. This product is dissolved in boiling ethyl acetate (210 cc); the solution is treated with decolorising charcoal (1 g) and filtered hot. The filtrate is cooled at a temperature of about 4° C. for 16 hours. The resulting crystals are filtered off, washed 3 times with ethyl acetate (30 cc in total) cooled to a temperature of about 4° C., and dried under reduced pressure (20 mm Hg; 2.7 kPa) at a temperature of about 20° C. in the presence of potassium hydroxide pellets. This gives 5-(4-benzylpiperazin-1-yl)pyrrolidin-2-one (9.78 g) in the form of white crystals melting at 160° C.

EXAMPLE 10

A mixture of 5-ethoxypyrrolidin-2-one (12.9 g) and 1-(3-trifluoromethylphenyl)piperazine (24.2 g) is heated for 35 minutes at a temperature between 155° C. and 164° C., with stirring, the ethanol formed being distilled off. After the reaction mixture has cooled, the solid obtained is filtered off, washed 4 times with diisopropyl ether (85 cc in total) and dried under reduced pressure (20 mm Hg; 2.7 kPa) at a temperature of about 20° C. in the presence of potassium hydroxide pellets. This gives a crude product (24.4 g) melting at 148°–150° C. This product is dissolved in boiling methanol (120 cc); the solution is treated with decolorising charcoal (1 g) and filtered hot. The filtrate is cooled at a temperature of about 4° C. for 16 hours. The resulting crystals are filtered off, washed twice with methanol (20 cc in total) and dried under reduced pressure (20 mm Hg; 2.7 kPa) at a temperature of about 20° C. in the presence of potassium hydroxide pellets. This gives 5-[4-(3-trifluoromethylphenyl)piperazin-1-yl]pyrrolidin-2-one (18.9 g) in the form of white crystals melting at 166° C.

EXAMPLE 11

A mixture of 5-ethoxypyrrolidin-2-one (6.45 g) and 1-(4-trifluoromethylphenyl)piperazine (10 g) is heated at a temperature of about 145° C. for 1 hour, with stirring, the ethanol formed being distilled off. After the reaction mixture was cooled, diethyl ether (10 cc) is added in order to suspend the solid obtained. The resulting crystals are then filtered off, washed 3 times with diethyl ether (25 cc in total) and dried in air. This gives a crude product (10.45 g) melting at 188° C. This product is dissolved in boiling ethanol (100 cc); the solution obtained is treated with decolorising charcoal (0.5 g) and filtered hot. The filtrate is cooled at a temperature of about 4° C. for 1 hour. The crystals obtained are filtered off, washed 3 times with ethanol (20 cc in total) cooled to a temperature of about 4° C., and dried under reduced pressure (20 mm Hg; 2.7 kPa) at a temperature of about 20° C. in the presence of potassium hydroxide pellets. This gives 5-[4-(4-trifluoromethylphenyl)-piperazin-1-yl]pyrrolidin-2-one (8.9 g) in the form of white crystals melting at 189° C.

EXAMPLE 12

A mixture of 5-ethoxypyrrolidin-2-one (8.5 g) and 1-(4-methylphenyl)piperazine (10.6 g) is heated for 1 hour 20 minutes at a temperature of about 140° C., with stirring, the ethanol formed being distilled off. After the reaction mixture has cooled, diethyl ether (20 cc) is added in order to suspend the solid obtained. The resulting crystals are then filtered off, washed 3 times with diethyl ether (60 cc in total) and dried under reduced pressure (20 mm Hg; 2.7 kPa) at a temperature of about 20° C. in the presence of potassium hydroxide pellets. This gives a product (11.3 g) melting at 202° C. This product is dissolved in boiling ethanol (340 cc). The solution obtained is treated with decolorising charcoal (0.5 g) and filtered hot. The filtrate is cooled at a temperature of about 4° C. for 16 hours. The resulting crystals are filtered off, washed twice with ethanol (20 cc in total) and twice with diethyl ether (50 cc in total) and then dried under reduced pressure (20 mm Hg; 2.7 kPa) at a temperature of about 20° C. in the presence of potassium hydroxide pellets. This gives 5-[4-(4-methylphenyl)piperazin-1-yl]pyrrolidin-2-one (10.4 g) in the form of white crystals melting at 204° C.

EXAMPLE 13

A mixture of 5-ethoxypyrrolidin-2-one (7.15 g) and 1-(3-methylphenyl)piperazine (9.75 g) is heated for 2 hours at a temperature of about 145° C., with stirring, the ethanol formed being distilled off. After the reaction mixture has cooled, acetonitrile (210 cc) is added and the mixture is heated to the reflux temperature in order to dissolve the solid obtained. The solution is treated with decolorising charcoal (0.5 g) and filtered hot. The filtrate is cooled at a temperature of about 4° C. for 1 hour. The resulting crystals are filtered off, washed 3 times with acetonitrile (25 cc in total) cooled to a temperature of about 4° C., and then 3 times with diisopropyl ether (45 cc in total) and then dried under reduced pressure (20 mm Hg; 2.7 kPa) at a temperature of about 20° C. in the presence of potassium hydroxide pellets. This gives 5-[4-(3-methylphenyl)piperazin-1-yl]pyrrolidin-2-one (9.8 g) in the form of cream-coloured crystals melting at 148° C.

EXAMPLE 14

A mixture of 5-ethoxypyrrolidin-2-one (7.1 g) and 1-(4-nitrophenyl)piperazine (10 g) is heated for 1 hour 40 minutes at a temperature between 130° C. and 143° C., with stirring, the ethanol formed being distilled off. After cooling, the reaction mixture is filtered and the solid obtained is washed 4 times with diethyl ether (55 cc in total) and dried under reduced pressure (20 mm Hg; 2.7 kPa) at a temperature of about 20° C. in the presence of potassium hydroxide pellets. This gives a crude product (13.9 g). This product is dissolved in boiling acetonitrile (500 cc); the solution is treated with decolorising charcoal (0.5 g) and filtered hot. The filtrate is cooled at a temperature of about 4° C. for 16 hours. The resulting crystals are filtered off, washed twice with acetonitrile (20 cc in total) and once with diethyl ether (25 cc) and then dried under reduced pressure (20 mm Hg; 2.7 kPa) at a temperature of about 20° C. in the presence of potassium hydroxide pellets. This gives 5-[4-(4-nitrophenyl)piperazin-1-yl]pyrrolidin-2-one (10.4 g) in the form of yellow crystals melting at 200° C.

EXAMPLE 15

A mixture of 5-ethoxypyrrolidin-2-one (7.1 g) and 1-(3p-methoxyphenyl)piperazine (9.25 g) is heated for 1 hour 20 minutes at a temperature between 132° C. and 148° C., with stirring, the ethanol formed being distilled off. After the reaction mixture has cooled, diethyl ether (25 cc) is added in order to suspend the solid obtained. The resulting crystals are then filtered off, washed 3 times with diethyl ether (45 cc in total) and dried under reduced pressure (20 mm Hg; 2.7 kPa) at a temperature of about 20° C. in the presence of potassium hydroxide pellets. This gives a crude product (12.2 g) melting at 140° C. This product is dissolved in boiling ethanol (150 cc). The solution obtained is treated with decolorising charcoal (0.5 g) and filtered hot. The filtrate is cooled at a temperature of about 4° C. for 4 hours. The crystals obtained are filtered off, washed 3 times with ethanol (30 cc in total) and dried under reduced pressure (20 mm Hg; 2.7 kPa) at a temperature of about 20° C. in the presence of potassium hydroxide pellets. This gives 5-[4-(3-methoxyphenyl)piperazin-1-yl]pyrrolidin-2-one (9.45 g) in the form of cream-coloured crystals melting at 156° C.

EXAMPLE 16

A mixture of 5-ethoxypyrrolidin-2-one (8.3 g) and 1-(4-hydroxyphenyl)piperazine (9.9 g) is heated at a temperature of about 127° C., with stirring, the ethanol formed being distilled off. Solidification is observed 15 minutes after the start of heating; xylene (40 cc) is then added in order to break up the reaction mixture, and heating is continued for 35 minutes at a temperature between 135° and 140° C. The suspension obtained is cooled to a temperature of about 40° C.; the solid is filtered off, washed once with xylene (10 cc) and 3 times with ethyl acetate (30 cc in total) and then dried under reduced pressure (20 mm Hg; 2.7 kPa) at a temperature of about 20° C. in the presence of potassium hydroxide pellets. This gives a crude product (13.95 g.). This product is dissolved in dimethylformamide (155 cc) at a temperature of about 110° C. The solution obtained is treated with decolorising charcoal (0.5 g) and filtered hot. The filtrate is cooled at a temperature of about 4° C. for 3 hours. The resulting crystals are filtered off, washed 3 times with dimethylformamide (30 cc in total) and 3 times with ethyl acetate (150 cc in total) and dried under reduced pressure (20 mm Hg; 2.7 kPa) at a temperature of about 20° C. in the presence of potassium hydroxide pellets. This gives 5-[4-(4-hydroxyphenyl)piperazin-1-yl]pyrrolidin-2-one (9.2 g) in the form of cream-coloured crystals melting at 270° C.

EXAMPLE 17

A mixture of 5-ethoxypyrrolidin-2-one (5.2 g) and 1-(3,4-dichlorophenyl)piperazine (8.1 g) is heated for 1 hour 30 minutes at a temperature between 100° C. and 140° C., with stirring, the ethanol formed being distilled off. After the reaction mixture has cooled, diethyl ether (20 cc) and ethanol (40 cc) are added. The resulting crystals are filtered off. After ethanol (40 cc) has been added to the filtrate, further crystals appear; they are filtered off, combined with those obtained previously, washed 3 times with diethyl ether (45 cc in total) and dried under reduced pressure (20 mm Hg; 2.7 kPa) at a temperature of about 20° C. in the presence of potassium hydroxide pellets. This gives a crude product (8.4 g). This product is dissolved in boiling ethanol (170 cc). The solution obtained is treated with decolorising charcoal (0.5 g) and filtered hot. The filtrate is cooled at a temperature of about 4° C. for 3 hours. The resulting crystals are filtered off, washed 3 times with ethanol (30 cc in total) and dried under reduced pressure (20 mm Hg; 2.7 kPa) at a temperature of about 20° C. in the presence of potassium hydroxide pellets. This gives 5-[4-(3,4-dichlorophenyl)piperazin-1-yl]pyrrolidin-2-one (6.5 g) in the form of white crystals melting at 186° C.

The 1-(3,4-dichlorophenyl)-piperazine can be prepared as described by L. THUNUS, C. L. LAPIERE and N. VERBEKE [Ann. Pharm. Fr., 38, 353 (1980)].

EXAMPLE 18

A mixture of 5-ethoxypyrrolidin-2-one (3.2 g) and 1-(4-dimethylaminophenyl)piperazine (4.4 g) is heated for 35 minutes at a temperature of about 145° C., with stirring. After the reaction mixture has cooled, the solid obtained is filtered off, washed 3 times with diethyl ether (60 cc in total) and dried in air. This gives a crude product (4.5 g) melting at 210° C. This product is dissolved in boiling ethanol (155 cc). The solution obtained is treated with decolorising charcoal (0.5 g) and filtered hot. The filtrate is cooled at a temperature of about 20° C. for 3 hours. The resulting crystals are filtered off, washed twice with ethanol (10 cc in total) and twice with diethyl ether (10 cc in total) and dried under reduced pressure (20 mm Hg; 2.7 kPa) at a temperature of about 20° C. in the presence of potassium hydroxide pellets. This gives 5-[4-(4-dimethylaminophenyl)piperazin-1-yl]pyrrolidin-2-one (2.9 g) in the form of cream-coloured crystals melting at 212° C.

The 1-(4-dimethylaminophenyl)piperazine can be prepared in the following manner:

A mixture of N,N-dimethyl-para-phenylenediamine dihydrochloride (25 g), bis-(2-chloroethyl)amine hydrochloride (21.4 g) and potassium carbonate (33.2 g) in 2-butoxyethanol (80 cc) is heated for 17 hours at a temperature of about 155° C., with stirring. After the reaction mixture has cooled, distilled water (400 cc) is added and the aqueous phase is washed three times with ethyl acetate (450 cc in total). The aqueous phase is brought to a pH of about 10 by adding a 10N aqueous solution of sodium hydroxide, saturated with sodium chloride, and then extracted a further 3 times with ethyl acetate (450 cc in total). The organic extracts are combined, dried over anhydrous magnesium sulphate, treated with decolorising charcoal (0.5 g) and filtered, and the filtrate is concentrated to dryness under reduced pressure (20 mm Hg; 2.7 kPa) at a temperature of about 40° C. This gives a product (21 g). This product is dissolved in ethanol (210 cc). The solution obtained is treated with a 7N solution of hydrogen chloride in ethanol (35 cc) and cooled at a temperature of about 4° C. for 2 hours. The resulting crystals are filtered off, washed 3 times with ethanol (75 cc in total) and twice with diethyl ether (100 cc in total) and then dried under reduced pressure (20 mm Hg; 2.7 kPa) at a temperature of about 20° C. in the presence of potassium hydroxide pellets. This gives a product (18 g) melting at 200°-205° C. This product is dissolved in distilled water (180 cc). The solution obtained is brought to a pH of about 11 by adding a 10N solution of sodium hydroxide (13 cc), saturated with sodium chloride, and extracted 4 times with ethyl acetate (400 cc in total). The organic extracts are combined, dried over anhydrous magnesium sulphate, treated with decolorising charcoal (0.5 g) and filtered, and the filtrate is concentrated to dryness under reduced pressure (20 mm Hg; 2.7 kPa) at a temperature of about 40° C. This gives a product (7.2 g). This product is chromatographed on a column of diameter 4 cm, containing silica (0.063-0.2 mm; 73 g), elution being carried out with methanol and 100 cc fractions being collected. The first fraction is discarded; the next 7 fractions are combined and concentrated to dryness under reduced pressure (20 mm Hg; 2.7 kPa) at a temperature of about 45° C. This gives 1-(4-dimethylaminophenyl)piperazine (4.5 g) in the form of a brown oil which crystallises [Rf=0.15; chromatography on a thin layer of silica gel; eluant:methanol].

EXAMPLE 19

A mixture of 5-ethoxypyrrolidin-2-one (4.5 g) and 4-(4-chloro-3trifluoromethylphenyl)piperazine (9.3 g) is heated for 1 hour at a temperature between 130° C. and 139° C., with stirring, the ethanol formed being distilled off. After cooling, the reaction mixture is diluted with ethanol (25 cc) and the solution obtained is stirred at a temperature of about 20° C. for 16 hours. A product precipitates; diethyl ether (25 cc) is then added to the reaction mixture; the resulting crystals are filtered off, washed 3 times with diethyl ether (60 cc in total) and dried under reduced pressure (20 mm Hg; 2.7 kPa) at a temperature of about 20° C. in the presence of potassium hydroxide pellets. This gives a crude product (6.2 g) melting at 152° C. This product is dissolved in boiling ethyl acetate (60 cc); the solution is treated with decolorising charcoal (1 g) and filtered hot. The filtrate is cooled at a temperature of about 4° C. for 3 hours. The resulting crystals are filtered off, washed twice with ethyl acetate (15 cc in total) and dried under reduced pressure (20 mm Hg; 2.7 kPa) at a temperature of about 20° C. in the presence of potassium hydroxide pellets. This gives 5-[4-(4-chloro-3-trifluoromethylphenyl)piperazin-1-yl]pyrrolidin-2-one (4.8 g) in the form of white crystals melting at 155° C.

EXAMPLE 20

A mixture of 5-ethoxypyrrolidin-2-one (4.7 g) and 4-(3,4,5-trimethoxyphenyl)piperazine (8.3 g) is heated for 1 hour at a temperature of about 140° C., with stirring, the ethanol formed being distilled off. After the reaction mixture was cooled, ethanol (20 cc) is added in order to suspend the solid obtained. The resulting crystals are then filtered off, washed 3 times with ethanol (6 cc in total) and dried under reduced pressure (20 mm Hg; 2.7 kPa) at a temperature of about 20° C. in the presence of potassium hydroxide pellets. This gives a crude product (3.1 g) melting at 138° C. The mother liquors from the crystallisation are concentrated to dryness under reduced pressure (20 mm Hg; 2.7 kPa) at a temperature of about 50° C. This gives a product (9.5 g) which is chromatographed on a column of diameter 3 cm, containing silica (0.04–0.063 mm; 240 g). Elution is carried out with a mixture of ethyl acetate and methanol (80/20 by volume) under a pressure of 0.5 bar (51 kPa), 50 cc fractions being collected. The first 10 fractions are discarded and the next 12 are combined and concentrated to dryness under reduced pressure (20 mm Hg; 2.7 kPa) at a temperature of about 50° C. This gives a product (3.4 g) melting at 130° C. This product is combined with the product obtained previously (3.1 g), and boiling ethyl acetate (80 cc) is added. The solution obtained is treated with decolorising charcoal (0.5 g) and filtered hot; the filtrate is cooled at a temperature of about 4° C. for 1 hour. The resulting crystals are filtered off, washed 3 times with ethyl acetate (20 cc in total) cooled to a temperature of about 4° C. and dried under reduced pressure (20 mm Hg; 2.7 kPa) at a temperature of about 20° C. in the presence of potassium hydroxide pellets. This gives 5-[4-(3,4,5-trimethoxyphenyl)piperazin-1-yl]pyrrolidin-2-one (4.5 g) in the form of cream-coloured crystals melting at 140° C.

EXAMPLE 21

A mixture of 5-ethoxypyrrolidin-2-one (8.5 g) and 1-(2-nitrophenyl)piperazine (9.1 g) is heated for 1 hour 30 minutes at a temperature of about 140° C., with stirring, the ethanol formed being distilled off. After the reaction mixture has cooled, diethyl ether (20 cc) is added in order to suspend the solid obtained. The resulting crystals are then filtered off, washed 3 times with diethyl ether (60 cc in total) and dried in air. This gives a crude product (12 g) melting at 196° C. This product is dissolved in boiling ethanol (575 cc). The solution obtained is treated with decolorising charcoal (0.5 g) and filtered hot. The filtrate is cooled at a temperature of about 4° C. for 48 hours. The crystals obtained are filtered off, washed 3 times with ethanol (45 cc in total) and dried under reduced pressure (20 mm Hg; 2.7 kPa) at a temperature of about 20° C. in the presence of potassium hydroxide pellets. This gives 5-[4-(2-nitrophenyl)piperazin-1-yl]pyrrolidin-2-one (10.3 g) in the form of orange crystals melting at 197° C.

EXAMPLE 22

Sodium borohydride (4.7 g) is added to a solution of 3-phenylpyrrolidine-2,5-dione (14.5 g) in ethanol (580 cc); the suspension obtained is immediately cooled to a temperature between 0° C. and −5° C. A 7.1N solution of hydrogen chloride in ethanol (11.7 cc) is then added over a period of 2 hours at a temperature between 0° C. and −5° C. The suspension is stirred at a temperature of about 0° C. for 2 hours 30 minutes. A further amount of a 7.1N solution of hydrogen chloride in ethanol (6 cc) is added and stirring is continued at a temperature of about 0° C. for 1 hour. A 10% (weight/volume) solution of potassium hydroxide in ethanol (50 cc) is then added and the reaction mixture is stirred at a temperature of about 20° C. for 16 hours. The solid obtained is filtered off and the filtrate is concentrated to dryness under reduced pressure (20 mm Hg; 2.7 kPa) at a temperature of about 45° C. The product obtained (19.7 g) is taken up in diethyl ether (190 cc) and the insoluble material is filtered off. The filtrate is concentrated to dryness under reduced pressure (20 mm Hg; 2.7 kPa) at a temperature of about 50° C. This gives a product (14 g). N-Phenylpiperazine (11 g) is added to this product and the solution obtained is heated at a temperature of about 140° C. for 45 minutes. After the reaction mixture has cooled, the solution obtained is diluted with methanol (50 cc) and then stirred at a temperature of about 20° C. for 3 hours. The resulting crystals are filtered off, washed twice with methanol (20 cc in total) and twice with diethyl ether (20 cc in total) and then dried under reduced pressure (20 mm Hg; 2.7 kPa) at a temperature of about 20° C. in the presence of potassium hydroxide pellets. This gives a product (9.6 g) melting at 158°–160° C. This product is dissolved in boiling ethanol (290 cc); the solution obtained is treated with decolorising charcoal (0.5 g) and filtered hot. The filtrate is cooled at a temperature of about 4° C. for 48 hours. The resulting crystals are filtered off, washed twice with ethanol (20 cc in total) and twice with diethyl ether (20 cc in total) and then dried under reduced pressure (20 mm Hg; 2.7 kPa) at a temperature of about 20° C. in the presence of potassium hydroxide pellets. This gives 3-phenyl-5-[4-phenylpiperazin-1-yl]pyrrolidin-2-one (7.3 g) in the form of white crystals melting at 174° C.

The 3-phenylpyrrolidine-2,5-dione can be prepared as described by R. WEGSCHEIDER and J. HECHT, Monatsh., 24, 422 (1903).

EXAMPLE 23

A mixture of 5-ethoxypyrrolidin-2-one (9 g) and 4-phenylpiperidine (8 g) is heated for 20 minutes at a temperature of about 140° C., with stirring, the ethanol formed being distilled off. After the reaction mixture has cooled, the solid obtained is filtered off, washed 3 times with ethyl acetate (25 cc in total) and dried under reduced pressure (20 mm Hg; 2.7 kPa) at a temperature of about 20° C. in the presence of potassium hydroxide pellets. This gives a crude product (10.7 g) melting at 198° C. This product is dissolved in boiling acetonitrile (430 cc). The solution obtained is treated with decolorising charcoal (0.5 g) and filtered hot. The filtrate is cooled at a temperature of about 4° C. for 4 hours. The resulting crystals are filtered off, washed 3 times with acetonitrile (30 cc in total) and dried under reduced pressure (20 mm Hg; 2.7 kPa) at a temperature of about 20° C. in the presence of potassium hydroxide pellets. This gives 5-(4-phenylpiperidino)-pyrrolidin-2-one (8.6 g) in the form of white crystals melting at 200° C.

EXAMPLE 24

A suspension of 5-(4-phenylpiperazin-1-yl)-pyrrolidin-2-one (19.6 g) in dimethylformamide (300 cc) is added over a period of 50 minutes, at a temperature between 22° C. and 28° C., to a suspension of sodium hydride (a 50% dispersion in vaseline oil; 4.6 g) in dimethylformamide (50 cc). The reaction mixture is stirred for two hours at a temperature of about 23° C. A solution of methyl iodide (12.4 g) in dimethylformamide (50 cc) is then added over a period of 15 minutes at a temperature between 23° C. and 33° C. After a further 16 hours of stirring at a temperature of about 20° C., the reaction mixture is filtered and the insoluble material is washed twice with dimethylformamide (100 cc in total). The filtrates are combined and concentrated to dryness under reduced pressure (5 mm Hg; 0.7 kPa) at a temperature of about 40° C. The product obtained is dissolved in distilled water (200 cc) at a temperature of about 50° C. After cooling to a temperature of about 20° C., the resulting crystals are filtered off, washed twice with distilled water (50 cc in total) cooled to a temperature of about 4° C., and then dried in air at a temperature of about 20° C. This gives a hydrated crude product (21 g) melting at a temperature of about 50° C. This product is dissolved in boiling diisopropyl ether (500 cc). The water which has appeared is separated off by decantation and the organic phase is filtered hot. After cooling at at temperature of about 4° C. for 2 hours, the resulting crystals are filtered off, washed 3 times with diisopropyl ether (150 cc in total) and dried under reduced pressure (20 mm Hg; 2.7 kPa) at a temperature of about 20° C. in the presence of potassium hydroxide pellets, and then dried to constant weight under 1 mm Hg (0.14 kPa) at 20° C. This gives a hydrated and hygroscopic product (15.3 g). When left in air until it reaches a constant weight, this product absorbs 500 mg of water. This finally gives 1-methyl-5-(4-phenylpiperazin-1-yl)pyrrolidin-2-one monohydrate in the form of white crystals melting at 84° C.

The 5-(4-phenylpiperazin-1-yl)pyrrolidin-2-one is prepared as in Example 1.

EXAMPLE 25

A suspension of 5-(4-phenylpiperazin-1-yl)-pyrrolidin-2-one (52 g) and 2,4-bis-(4-methoxyphenyl)-1,3,2-4-dithiadiphosphetane-2,4-dithione (53.5 g) in 1,2-dimethoxyethane (1000 cc) is stirred at a temperature of about 20° C. for 24 hours. The resulting crystals are filtered off, washed twice with 1,2-dimethoxyethane (100 cc in total) and 3 times with diisopropyl ether (300 cc in total) and dried under reduced pressure (20 mm Hg; 2.7 kPa) at a temperature of about 20° C. in the presence of potassium hydroxide pellets. This gives a crude product (8.4 g) melting at 200° C. This product (8 g) is combined with the product prepared in the same manner in a previous operation (0.3 g) and dissolved in boiling ethanol (800 cc). Decolorising charcoal (0.5 g) is added and the mixture is filtered hot; the filtrate is cooled at a temperature of about 4° C. for 1 hour. The crystals obtained are filtered off, washed 3 times with ethanol (150 cc in total) and then 3 times with diethyl ether (150 cc in total) and dried under reduced pressure (20 mm Hg; 2.7 kPa) at a temperature of about 20° C. in the presence of potassium hydroxide pellets. The product thus obtained (6.3 g) is dissolved in boiling butan-1-ol (120 cc). After cooling at a temperature of about 20° C. for 1 hour, the resulting crystals are filtered off, washed twice with butan-1-ol (20 cc in total), then 3 times with ethanol (75 cc in total) and finally 3 times with diethyl ether (75 cc in total) and dried under reduced pressure (20 mm Hg; 2.7 kPa) at a temperature of about 20° C. in the presence of potassium hydroxide pellets. This gives 5-(4-phenylpiperazin-1-yl)pyrrolidine-2-thione (5.6 g) in the form of white crystals melting at 210° C.

The 5-(4-phenylpiperazin-1-yl)pyrrolidin-2-one is prepared as indicated in Example 1.

The present invention includes within its scope pharmaceutical compositions which comprise as active ingredient, at least one pyrrolidine derivative of general formula I or a pharmaceutically-acceptable acid addition salt thereof, in association with any other pharmaceutically compatible product, which can be inert or physiologically active. The compositions according to the invention can be administered orally, parenterally or rectally.

Tablets, pills, powders (in particular, in gelatin capsules or in cachets) or granules can be used as solid compositions for oral administration. In these compositions, the active compound according to the invention is mixed with one or more inert diluents such as starch, cellulose, sucrose, lactose or silica. These compositions can also comprise substances other than diluents, e.g. one or more lubricants such as magnesium stearate or talc, a colorant, a coating (coated tablets) or a lacquer.

Pharmaceutically acceptable elixirs, solutions, suspensions, emulsions and syrups, containing inert diluents such as water, ethanol, glycerol, vegetable oils or paraffin oil, can be used as liquid compositions for oral administration. These compositions can also comprise substances other than diluents, e.g. wetting agents, sweeteners, thickeners, flavourings or stabilisers.

Sterile compositions for parenteral administeration are preferably suspensions, emulsions or aqueous or non-aqueous solutions. Water, propylene glycol, a polyethylene glycol, vegetable oils, in particular olive oil, injectable organic esters, e.g. ethyl oleate, or other suitable organic liquids can be employed as the solvent or vehicle. These compositions can also contain adjuvants, in particular wetting agents, agents for creating isotonicity, emulsifiers, dispersants and stabilisers. Sterilisation can be carried out in several ways, e.g. by filtration under aseptic conditions, by incorporating sterilising agents into the composition, by irradiation or by heating. The compositions can also be prepared in the form of sterile solid compositions which can be dissolved in an injectable sterile medium at the time of use.

Compositions for rectal administration are suppositories or rectal capsules, which contain, in addition to the active compound, excipients such as cocao butter, semi-synthetic glycerides or polyethylene glycols.

In human therapy, the pyrrolidine compounds according to the invention are particularly useful for treating the syndromes of various depressive states and of psychasthenic states. The doses depend on the desired effect and the duration of the treatment; for an adult, they are generally between 10 and 300 mg per day, administered orally or subcutaneously in one or more portions.

In general, the physician will determine the posology which he considers to be most appropriate, taking into account the age, the weight and all other factors intrinsic to the patient to be treated.

The following Examples illustrate pharmaceutical compositions according to the invention.

EXAMPLE 26

Tablets containing 10 mg doses of active product and having the following composition are prepared according to the usual technique:

| | |
|---|---|
| 5-(4-phenylpiperazin-1-yl)pyrrolidine-2-thione | 10 mg |
| starch | 60 mg |
| lactose | 50 mg |
| magnesium stearate | 2 mg |

EXAMPLE 27

Ampoules each containing 10 mg of active product are prepared by making up a solution containing:

| | |
|---|---|
| 5-[4-(4-methoxyphenyl)-piperazin-1-yl]-pyrrolidin-2-one | 100 mg |
| 0.1 N aqueous solution of hydrochloric acid | 3.65 cc |
| distilled water q.s. | 20 cc | and then by dividing up the resulting solution equally into 10 ampoules.

We claim:

1. A pyrrolidine of the formula:

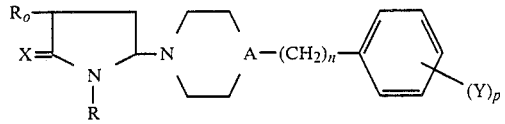

wherein X represents an oxygen or sulphur atom, R represents a hydrogen atom or an alkyl radical, $R_o$ represents a hydrogen atom, an alkyl radical, a phenyl radical, or a phenyl radical substituted by one halogen atom or by one alkyl, alkoxy, alkylthio or nitro radical, A represents a nitrogen atom or a radical =CH—, the symbol Y represents a hydrogen or halogen atom or an alkyl, alkoxy, alkylthio, alkylcarbonyl, nitro, amino, alkylcarbonylamino, alkylamino, dialkylamino, alkylsulphinyl, alkylsulphonyl, alkoxycarbonyl, cyano, trifluoromethyl, hydroxy, mercapto, alkylcarbonyloxy or alkylcarbonylthio radical, n represents zero or 1, and p represents 1, 2 or 3, it being understood that the alkyl and alkoxy radicals, and alkyl and alkoxy moieties of any of the aforementioned groups, contain from 1 to 4 carbon atoms, and when p represents 2 or 3 the atoms or radicals represented by the symbols Y may be the same or different, p having a maximum value of 2 when Y is nitro or hydroxy, or a non-toxic pharmaceutically-acceptable acid addition salt thereof.

2. A pyrrolidine according to claim 1 wherein X represents an oxygen or sulphur atom, R represents a hydrogen atom or an alkyl radical, $R_o$ represents a hydrogen atom, A represents a nitrogen atom, Y represents a hydrogen or halogen atom or an alkyl, alkoxy, alkylthio, alkylcarbonyl, nitro, amino, alkylcarbonylamino, alkylamino, dialkylamino, alkylsulphinyl, alkylsulphonyl, alkoxycarbonyl, cyano, trifluoromethyl, hydroxy, mercapto, alkylcarbonyloxy or alkylcarbonylthio radical, n represents zero or 1, and p represents 1, 2 or 3, p having a maximum value of 2 when Y is nitro or hydroxy, or a non-toxic pharmaceutically-acceptable acid addition salt thereof.

3. A pyrrolidine according to claim 1 wherein X represents an oxygen or sulphur atom, $R_o$ represents a hydrogen atom, R represents a hydrogen atom or an alkyl radical, A represents a nitrogen atom or a radical =CH—, Y represents a hydrogen or halogen atom or an alkyl, alkoxy, alkylcarbonyl, nitro or trifluoromethyl radical, n represents zero or 1, and p represents 1, or a non-toxic pharmaceutically-acceptable acid addition salt thereof.

4. A pyrrolidine according to claim 1 wherein X represents an oxygen atom, $R_o$ and R each represent a hydrogen atom, A represents a nitrogen atom, Y represents a hydrogen or halogen atom or an alkyl, alkoxy, alkylcarbonyl or nitro radical, n represents zero, and p represents 1, or a non-toxic pharmaceutically-acceptable acid addition salt thereof.

5. A pyrrolidine according to claim 1 which is 5-(4-phenylpiperazin-1-yl)pyrrolidin-2-one or a non-toxic pharmaceutically-acceptable acid addition salt thereof.

6. A pyrrolidine according to claim 1 which is 5-[4-(2-methylphenyl)piperazin-1-yl]pyrrolidin-2-one or a non-toxic pharmaceutically-acceptable acid addition salt thereof.

7. A pyrrolidine according to claim 1 which is 5-[4-(4-chlorophenyl)piperazin-1-yl]pyrrolidin-2-one or a non-toxic pharmaceutically-acceptable acid addition salt thereof.

8. A pyrrolidine according to claim 1 which is 5-[4-(4-methoxyphenyl)piperazin-1-yl]pyrrolidin-2-one or a non-toxic pharmaceutically-acceptable acid addition salt thereof.

9. A pyrrolidine according to claim 1 which is 5-[4-(4-acetylphenyl)piperazin-1-yl]pyrrolidin-2-one or a non-toxic pharmaceutically-acceptable acid addition salt thereof.

10. A pyrrolidine according to claim 1 which is 5-[4-(3-trifluoromethylphenyl)piperazin-1-yl]pyrrolidin-2-one or a non-toxic pharmaceutically-acceptable acid addition salt thereof.

11. A pyrrolidine according to claim 1 which is 5-[4-(4-nitrophenyl)piperazin-1-yl]pyrrolidin-2-one or a non-toxic pharmaceutically-acceptable acid addition salt thereof.

12. A pharmaceutical composition which comprises an effective amount of a pyrrolidine as claimed in claim 1, or a non-toxic pharmaceutically-acceptable acid addition salt thereof, in association with a pharmaceutical carrier.

13. A method for the treatment of a patient suffering from depression which comprises administering to the patient an amount of a pyrrolidine as claimed in claim 1, or a non-toxic pharmaceutically-acceptable acid addition salt thereof, sufficient to improve the condition of the patient.

14. A method according to claim 13 in which the patient is an adult and from 10 to 300 mg of said pyrrolidine, or a non-toxic pharmaceutically-acceptable acid addition salt thereof, is administered to the patient per day.

* * * * *